Figure 1:
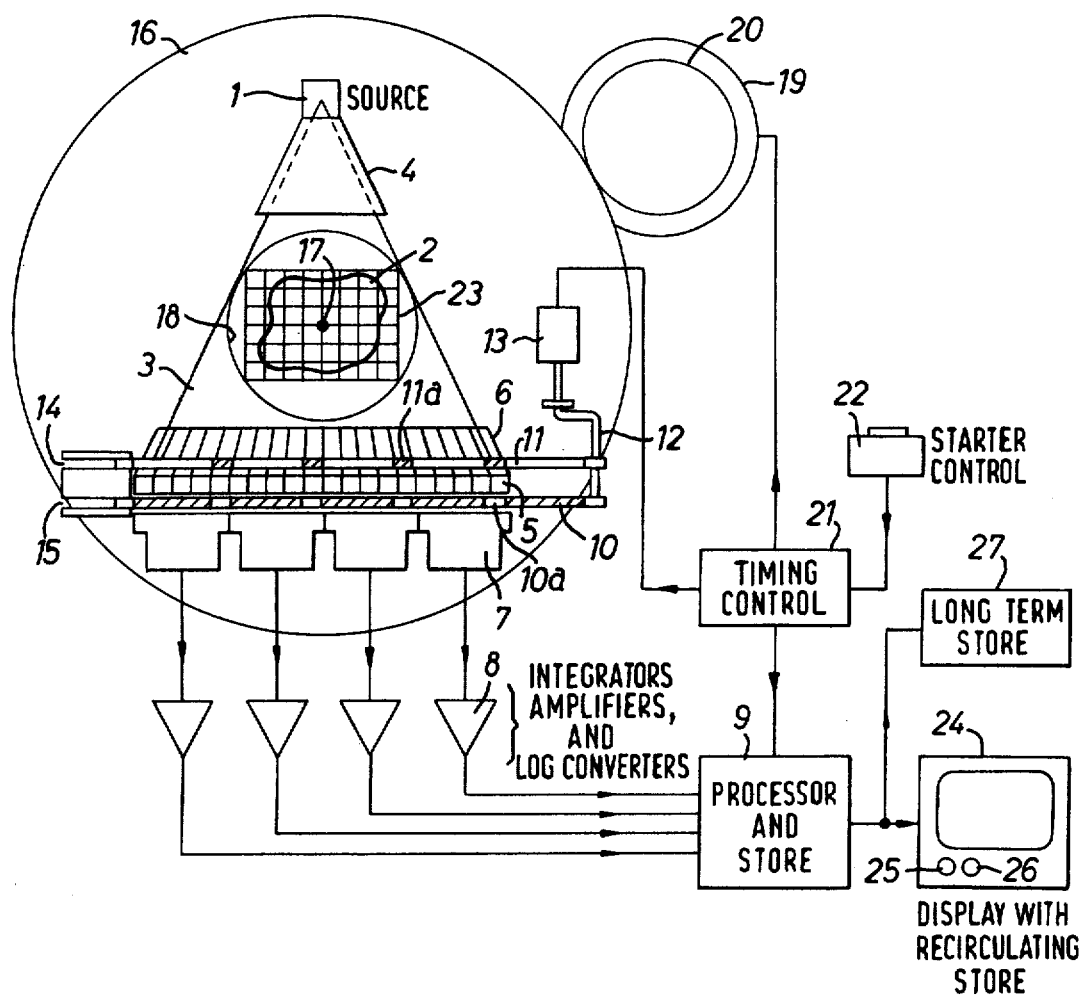

United States Patent [19]

Hounsfield

[11] 3,940,626

[45] Feb. 24, 1976

[54] DETECTION OF RADIATION IN RADIOGRAPHIC APPARATUS

[75] Inventor: Godfrey Newbold Hounsfield, Newark, England

[73] Assignee: E M I Limited, Hayes, England

[22] Filed: Apr. 24, 1974

[21] Appl. No.: 463,829

[30] Foreign Application Priority Data
May 5, 1973 United Kingdom............. 21525/73

[52] U.S. Cl................................. 250/366; 250/369
[51] Int. Cl.².......................................... G01T 1/20
[58] Field of Search......... 250/363, 366, 369, 445 T

[56] References Cited
UNITED STATES PATENTS

| | | | |
|---|---|---|---|
| 2,730,566 | 1/1956 | Bartow et al. | 250/369 X |
| 3,101,407 | 8/1963 | Shipman, Jr. | 250/363 |
| 3,774,030 | 11/1973 | O'Connor et al. | 250/363 X |

*Primary Examiner*—Archie R. Borchelt
*Attorney, Agent, or Firm*—Fleit & Jacobson

[57] ABSTRACT

The invention provides apparatus for examining bodies by means of penetrating radiation such as X- or γ-radiation. The radiation is directed toward the body in a sectoral-shaped swath and the radiation emergent from the body is collected by detector devices. Each device comprises a scintillator crystal which is arranged to respond to the receipt of the radiation by emitting visible light. The devices are irradiated simultaneously and then interrogated in sequence so that the light emitted by respective ones of the devices, which is in each case indicative of the amount of radiation incident thereon, can be identified as to its origin.

8 Claims, 5 Drawing Figures

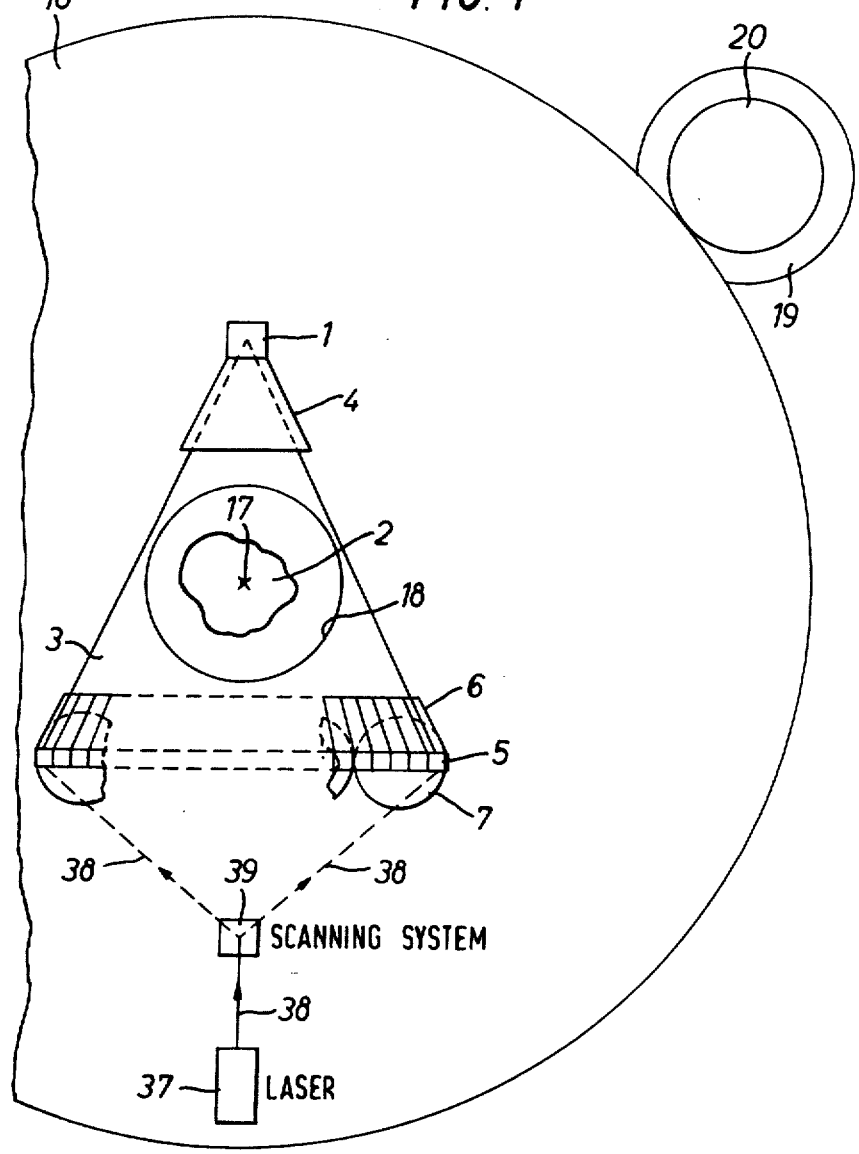

DETECTION OF RADIATION IN RADIOGRAPHIC APPARATUS

The present invention relates to radiography and it relates especially, although not exclusively, to the technique of examining a body by means of radiation such as X- or γ-radiation which is disclosed and claimed in our British Patent Specification No. 1,283,915.

The aforementioned technique involves directing radiation through part of a body along a plurality of sets of rays, and detecting the radiation emergent from the body along each of said rays to provide so-called "edge readings" from which the absorption suffered by each ray can be determined. Each set of rays contains a plurality of co-planar rays which are parallel to one another or, alternatively, mutually divergent and each set of rays is directed through the body from a respective angular orientation with respect thereto; the sets of rays being co-planar.

The planar part of the body through which the rays are directed is notionally delineated into a two-dimensional matrix of elements, the size of said elements being related to the width of the individual rays and the spacing between adjacent rays of a set. The number of angular orientations around said body from which rays are directed therethrough multiplied by the number of rays in each set is arranged to be greater than the number of elements in the matrix so that by suitable processing of said edge readings the absorption (or transmission) coefficients of the elements of the matrix can be determined.

This invention is concerned with the derivation of said edge readings.

According to the invention there is provided a radiographic apparatus for examining a body by means of radiation such as X- or γ-radiation including, a. a source of said radiation arranged to irradiate a substantially planar slice of the body along a plurality of similar sets of rays, each set being directed through said body at a respective angle, or mean angle, with respect thereto b. detecting means, disposed on the side of the slice remote from the source, for detecting the radiation transmitted through the body along each of the rays; said detecting means including i. a detector device arranged to receive radiation transmitted alonge one of the rays of a set and to provide output energy, of a wavelength different from that of the radiation, which is indicative of the amount of radiation received thereby and
  ii. measuring means arranged to measure the intensity of said output energy, c. switching means for causing the measuring means to measure said output energy over a predetermined interval of time and d. means for substantially preventing the radiation being incident on the detector device during the predetermined interval.

Figure 2:
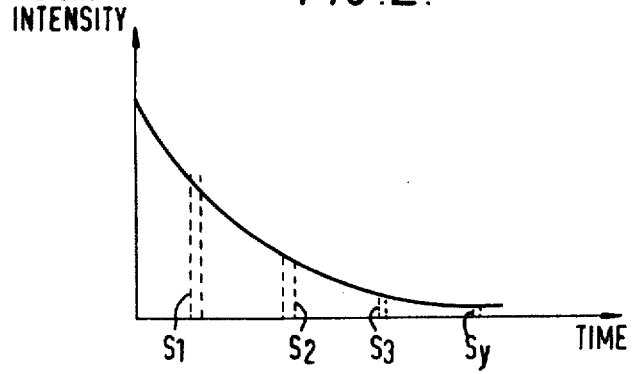
Figure 3A:
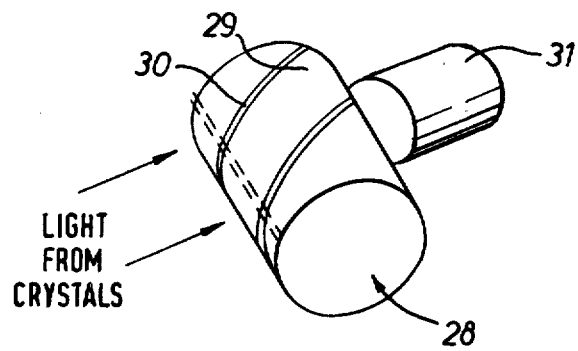
Figure 3B:
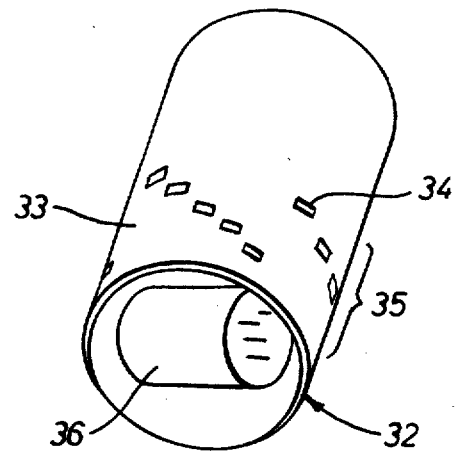

In order that the invention may be clearly understood and readily carried into effect, some embodiments thereof will now be described by way of example only with reference to the accompanying drawings of which:

FIG. 1 shows, in schematic plan view, apparatus in accordance with one example of this invention, FIG. 2 shows a graph explanatory of the operation of the invention, FIG. 3a and 3b show respectively alternative constructions which may be used for the oscillating scanning system shown in FIG. 1, and FIG. 4 shows, in schematic plan view, apparatus in accordance with a second example of this invention.

Referring now to FIG. 1, radiation from a source 1 is directed through a body 2 in a planar, sectoral swath 3 which is defined by a collimator 4. On the side of the body 2 remote from the source 1 there is disposed a bank of $n$ radiation detecting crystals 5, each crystal being arranged, by means of respective collimators such as 6, to receive the radiation directed through the body along a respective one of a set of $n$ rays. In this example $n$ takes the value twenty, but this is for purposes of clarity of the drawing only and in practice a more typical value for $n$ is 300.

The crystals 5 are arranged to convert the received radiation into energy having its wavelength in the visible band of the spectrum and to store such energy for a predetermined period. A typical storage period in this example is one millisecond.

Associated with each sub-set of $p$ adjacent crystals 5 is a single photomultiplier such as 7; and in this example $p$ takes the value 5. In the above-mentioned practical example, where $n$ is 300, $p$ might take the value 30.

Output signals from the photomultipliers such as 7 represent the aforementioned edge readings, and these signals are amplified and converted into logarithmic values in respective circuits such as 8 and all the circuits such as 8 are arranged to feed a processor and store 9. It will be appreciated that, with the apparatus thus far described, an output signal from any of the photomultipliers such as 7 would relate to the light outputs of all $p$ crystals in the relevant sub-set. Thus a given output would be a confused combination of $p$ edge readings relating to $p$ rays. It is, however, desirable for the $p$ crystals to "share" one photomultiplier because this arrangement is more economical in components than an arrangement in which each crystal communicates with a respective photomultiplier and also practical difficulties of obtaining, packing in and connecting up large number of small, individually screened, photomultipliers are avoided.

In order to permit a single photomultiplier to provide distinguishable output signals relating to the light outputs of $p$ crystals, an apertured shutter member 10, which is opaque apart from $(n/p)$ apertures such as 10a which apertures are of the dimensions of the output face of a single crystal, is oscillated to and fro between the bank of crystals 5 and the photomultipliers 7. The arrangement is such that as the shutter member 10 oscillates to and fro the apertures permit light from corresponding ones of the crystals of each sub-set to impinge sequentially on the respective photomultipliers 7. The output signals from respective crystals-and therefore the edge reading from respective rays - can thus be separated on a time basis.

It has been found that when a quantum of X- or γ-ray energy impinges on a given crystal, a scintillation of high brilliance and short duration occurs and is emitted from the crystal. If, at this time, one of the apertures 10a in the shutter member 10 is interposed between that crystal and its respective photomultiplier, an electrical impulse of correspondingly high amplitude is produced by the photomultiplier. Such an impulse represents an undesirable form of noise, since it bears substantially no relationship to the mean absorption of radiation suffered by the ray in question. In order to prevent such an occurrence, a second shutter member 11, which is arranged to move synchronously with the member 10, is provided between the collimators 6 and the crystals 5. The member 11 is arranged to be transparent to the radiation from source 1 over most of its length, but is provided with ($n/p$) segments such as 11a which are opaque, or substantially so, to said radiation. The segments 11a are of similar dimensions to the apertures 10a and the arrangement is such that when an aperture 10a of member 10 is interposed between a given crystal and the relevant photomultiplier, a segment 11a of the member 11 is disposed in front of the crystal so as to prevent radiation from impinging thereupon whilst its optical output is being detected by the photomultiplier.

Suitably the two shutter members 10 and 11 are driven, by a common crank arrangement shown schematically at 12, from an electrical motor 13. In order to improve the linearity of the reciprocating motion of the shutter members 10 and 11, an arrangement for introducing third harmonic distortion into the substantially sinusoidal motion of said members, can be used. Linear runner bearings 14 and 15 are provided to guide the members 10 and 11 and to constrain their motion to the desired to and fro reciprocation.

The components thus far described, with the exceptions of the amplifier and logarithmic converter circuits 8 and the processor and store 9, are mounted on an apertured turntable 16 which can rotate about a central axis 17. The body 2 is situated within the aperture 18 in the turntable 16 and is, in this example arranged to be surrounded with water so as to reduce discontinuities in absorption suffered by the radiation in the vicinity of the body 2. The body 2 is protected from the water by means of a rubber enclosure (not shown) which fits tightly around said body. It will be appreciated that the body 2 remains stationary and that the turntable 16 can rotate around it.

The turntable 16 is rotatable in angular steps of about one degree by means of a second electrical motor 19, to the shaft of which is attached a drive member 20 which may constitute, for example a gear wheel adapted to co-operate with gear teeth provided around the periphery of the turntable 16.

The various operations of the motors 13 and 19 and of the processor and store 9 are controlled under the influence of a timing control circuit 21 which causes a predetermined cycle of operations to be effected consequent upon receiving a start pulse from a starter control circuit 22.

The arrangement is such that, with the turntable in the angular position shown in FIG. 1, the motor 13 is energised to cause the members 10 and 11 to oscillate to and fro about four times, for a reason which will become clear hereinafter. The output signals from the circuit 8 are segmented in the processor 9 under the influence of timing control circuit 21 and assigned to respective storage locations in the unit 9 in dependence upon which rays they were derived from. Signals relating to the same ray are summed in the unit 9. The timing control circuit 21 then energises the motor 19 and the turntable 16 is thus stepped angularly through (say) 1°. The members 10 and 11 are then caused to repeat their multi-pass oscillation and signals relating to the respective rays are stored in unit 9 as previously described. It is preferable for the motor 13 to rotate continuously and it can be arranged (though this is not shown in the drawing) for a shutter member to interrupt the beam 3 each time the turntable 16 is rotated through an angular step so that readings which are confused by the angular motion of the turntable 16 are avoided. The above sequence of operations is continued until the turntable has been rotated through an angle approaching 180°. When this has been done, the processor and store 9 is effective to process the information, for example as described in the aforementioned Patent Specification, to determine the absorption coefficients of all the elements in a notional, two dimensional matrix 23 of such elements which is delineated in said body. As will be seen from FIG. 1, the matrix 23 can extend into the water which surrounds the body 2 but does not extend beyond said water.

The oscillation of the members 10 and 11 can, if desired, be made sufficiently great that, at the extremities of such oscillations, light passing through an aperture 10a, in the member 10, associated with a particular photomultiplier is swept on to an adjacent photomultiplier. This enables relative calibration as between adjacent detectors to be effected. Moreover, in order ti closely control the passage of light from the crystals to the photomultipliers, additional collimating means can be provided between the member 10 and the photomultipliers.

The resulting output signals from the unit 9 are rendered visible on a cathode ray tube display 24 which has facilities for photographing the representation displayed on the screen thereof and which also includes a recirculatory store in order that the information to be displayed may be continuously re-applied to the display 24 at a rate sufficiently fast to avoid flicker of the representation. The display 24 includes a pair of controls 25 and 26 which are adapted to control the width and absolute position respectively of the range of absorption coefficients to be displayed on the screen of unit 24, This arrangement is similar to that provided in the aforementioned Patent Specification and is more fully described therein.

The information from unit 9 is also applied to a "permanent" or long-term store 27 wherein the information is recorded on a suitable storage medium, for example a magnetic tape or disc, or in punched paper tape or card form. The store of unit 9 can then be erased and re-used for new information.

The crystals 5 are arranged to exhibit storage characteristics of the kind shown in FIG. 2 in response to the receipt of incident radiation; the starting level for the decay curve shown in FIG. 2 being dependent upon the amount of absorption suffered by the radiation in its passage to the crystal. The four pairs of vertical dotted lines represent intervals when the respective aperture 10a of shutter member 10 is interposed between the crystal 5 and its photomultiplier 7. These intervals represent sampling intervals and they are thus labelled $S_1$, $S_2$, $S_3$ and $S_4$ respectively. The output signals from the photomultiplier 7 at each of the instants $S_1$ to $S_4$ are summed in unit 9 since they relate to the same ray passing through the body 2, and by this means an increase in accuracy is obtained since large signals are accumulatad. It may, of course, arise that the first sampling instant $S_1$ occurs when a crystal has not received a radiation quantum for an appreciable time. In this case, the output signal derived at instant $S_1$ would be low, but since the crystal output is sampled four times it is likely that a radiation quantum will be received before the end of the overall sampling period and thus it is correspondingly likely that one of the later sampling periods will provide a substantial output signal.

It will be evident to those skilled in the art that the shutter members 10 and 11 need not take the form shown in FIG. 1, and two alternative forms of shutter member are shown in FIG. 3.

FIG. 3a shows, in perspective view, an alternative form of shutter which could be used to replace the shutter 10. The shutter comprises a cylindrical rod 28 of transparent material, such as that known by the Registered Trade Mark "Perspex". The rod may be solid, as shown, or hollow but in either event its surface area 29 is rendered opaque, apart from a continuous helical track 30. A photomultiplier tube 31 is disposed as shown with its longitudinal axis perpendicular to and intersecting that of the rod 28. The pitch of the helical track 30 is made such that light from the crystals (not shown) which is incident on the part of the surface area of rod 28 marked by the two dashed lines is transmitted to the photomultiplier 31 provided that it is incident on part of the track 30. Thus it will be seen that, if the rod 28 rotates, the field of view of the photomultiplier 31 will be scanned across the crystals in a direction parallel to the axis of the rod 28. It will be appreciated that other photomultipliers will be provided adjacent and parallel with the photomultiplier 31 and that the rod 28 will be axially extended so as to allow for this; the system shown being a simple one for the purposes of illustration only. The rod 28 may be rotated by means of a respective motor (not shown) which can be controlled by the timing control circuits 21 (FIG. 1). Alternatively, if the oscillating shutter member 11 (FIG. 1) is provided, as is preferable, the rod 28 may be rotated, by means of a suitable arrangement of gears, by the same motor (13) as is used to drive the shutter 11.

In order to prevent stray light from affecting the photomultipliers it will be appreciated that the rod 28 and the photomultipliers such as 31 should be enclosed within a substantially light proof housing (not shown) which is provided with an entrance slit for permitting the light from the crystals to fall upon the rod 28 between the two dashed lines shown in FIG. 3a.

Referring now to FIG. 3b, an alternative arrangement to that shown in FIG. 3a is illustrated. In this arrangement, a hollow rod 32 of transparent material such as Perspex (Registered Trade Mark) is provided on its outer surface area 33 with an opaque coating. Apertures 34 are formed in said opaque coating and said apertures are arranged to align with respective crystals (not shown). The apertures 34 are disposed in a band 35 of the rod 32 and, in this example, they are designed to co-operate with one of the sub-sets of p crystals in FIG. 1. A photomultiplier tube 36 is mounted within the rod 32, its axis being perpendicular to and intersecting the axis of the rod 32, and the rod 32 is caused to rotate while the tube 36 remains stationary. Light from the crystals is caused to be incident upon the outer surface of the rod 32 in a strip such as that shown by the two dashed lines in FIG. 3a. The tube 36 is disposed such that said strip would fall directly upon its sensitive surface if the rod 32 were not interposed between the light and said surface. However it will be appreciated that as the rod 32 rotates, successive ones of the apertures 34 are interposed between the light and said surface of tube 36 so that the light output from each crystal of the sub-set can be detected in turn by the tube 36 and that a scan of the crystals is thus effected. It will be observed that more than one scan of the crystals can be undertaken with a single revolution of the rod 32 by providing more than one series of apertures 34 in the band 35 of rod 32. In the example shown in FIG. 3b, four series of apertures were provided so that the four scans referred to in the description of FIG. 1 can be achieved with one revolution of the rod 32. It will be appreciated that in this example there are five apertures 34 in a series because, as per the FIG. 1 arrangement, there are five crystals in a sub-set. Moreover apertures are shown in one band only of the rod 32 but, in this example, there would be four bands of apertures, each containing four series of five apertures. The rod 32 should be enclosed within a substantially light-proof housing (not shown) which includes a slit to enable light to be incident on the rod 32 as hereinbefore described.

The arrangement of FIG. 4 is generally similar to that of FIG. 1 and so FIG. 4 includes less detail than FIG. 1; similar features included in both FIGS. 1 and 4 are identified by the same reference numerals in each case.

As in FIG. 1, X- or γ-radiation from the source 1 is directed through the body 2 along a plurality of sets of rays, the rays of a set being defined by collimators 6 which communicate with respective crystals 5. However, the crystals 5 in this example are such as to store the energy incident thereon until irradiated by a strong infra-red beam, at which time optical energy, indicative of the stored energy, is liberated. Thus, a laser 37 is arranged to produce a fine beam 38 of infra-red energy and a scanning system 39 is arranged to scan the beam 38 over the crystals 5 in a predetermined sequence. In this example, it will be recalled, there are four sub-sets of five crystals, each sub-set being arranged to communicate with a respective photomultiplier tube 7. Thus the infra-red beam 38 is split, in the scanning means 39, into four component beams and the four component beams are scanned synchronously over respective ones of the sub-sets of crystals. By this means the information is liberated in a similar sequence to that achieved with the arrangement of FIG. 1

The scanning system 39 may, for example, comprise a rotatable mirror drum (not shown), the drum being, for example, of hexagonal form and bearing on each flat surface a plane mirror. Other suitable scanning devices could be used, however, such as the arrangement shown in our British Patent Specification No. 1,304,363, in which no moving parts are required.

The arrangement shown in FIG. 4 can be initially calibrated by replacing the body 2 with a box, having parallel sides constructed of Perspex (Registered Trade Mark) containing water, and storing the edge readings obtained from one or from a mean of several scans. These readings are then used as scaling factors for each crystal element taken along the scan.

It will be noted that, in the arrangement of FIG. 4, the photomultiplier tubes such as 7 are disposed beneath the bank of crystals 5 so that the infra red beam 38 can be scanned in a horizontal plane over the crystals. The turntable 16 can be provided with apertures through which the photomultipliers such as 7 can depend.

In all of the arrangements described hereinbefore, it is desirable that the extreme crystals of two adjacent sub-sets can provide signals to the photomultipliers respective to each of the sub-sets so that the gains of the photomultipliers can be equalised.

In FIG. 1 arrangement, it can be advantageous to activate the crystals 5 by means of a stationary infrared flood beam which is incident thereon via the shutter member 10. In this event, the photomultipliers 7 are preferably disposed below the array of crystals as shown in FIG. 4

Instead of processing the edge readings in the manner described with reference to the said British Patent Specification No. 1,283,915, any other suitable processing technique may be utilised.

What I claim is:

1. Radiographic apparatus for examining a body by means of radiation such as X- or γ-radiation including,
   a. a source of said radiation arranged to irradiate a substantially planar slice of the body along a plurality of similar sets of rays, each set being directed through said body at a respective angle, or mean angle, with respect thereto
   b. detecting means, disposed on the side of the slice remote from the source, for detecting the radiation transmitted through the body along each of the rays; said detecting means including
      i. a detector device arranged to receive radiation transmitted along one of the rays of a set and to provide output energy, of a wavelength different from that of the radiation, which is indicative of the amount of radiation received thereby and
      ii. measuring means arranged to measure the intensity of said output energy,
   c. switching means for causing the measuring means to measure said output energy over a predetermined interval of time and
   d. means for substantially preventing the radiation being incident on the detector device during the predetermined interval.

2. Apparatus according to claim 1 wherein each of said detector device comprises a scintillator crystal.

3. Apparatus according to claim 1 wherein the measuring means is arranged to measure, over different intervals of time, the output energy from five detector devices each receiving radiation along a different one of said rays.

4. Apparatus according to claim 1 wherein the measuring means is arranged to measure the output energy from said detector device four times for one of said rays.

5. Apparatus according to claim 1 wherein said switching means includes
   a. apertured shutter means, having an aperture for said detector device, interposed between said detector device and said measuring means, and
   b. means for causing said shutter means to move to and fro, relative to the detector device and measuring means, in the plane of the said slice of the body.

6. Apparatus according to claim 5 wherein said apertured shutter means comprises a rod member formed of material substantially transparent to said output energy, the surface of said rod member, apart from a continuous, helical track thereon, being rendered substantially opaque to said output energy.

7. Apparatus according to claim 1 wherein said means for preventing includes a shutter means disposed in front of the detector device and bearing a portion which is substantially opaque to the radiation, said shutter means being arranged to move synchronously with the operation of the switching means so that, when the measuring means is measuring the output energy from the detector means, the opaque portion of the shutter means is disposed to intercept radiation directed towards the detector device.

8. Apparatus according to claim 5 wherein the apertured shutter means comprises a hollow cylinder arranged to surround the measuring means, said cylinder having a surface rendered substantially opaque to said output energy apart from the aperture via which the output energy can impinge on the measuring means.

* * * * *